United States Patent [19]
Zlotnik et al.

[11] Patent Number: 5,816,846
[45] Date of Patent: Oct. 6, 1998

[54] ELECTRICAL CONNECTOR

[75] Inventors: Arnold H. Zlotnik, Pittsburgh; John A. Austin, Bakerstown; Milton Zlotnik, West Homstead, all of Pa.

[73] Assignee: Pestco, Inc., Pittsburgh, Pa.

[21] Appl. No.: 470,234

[22] Filed: Jun. 6, 1995

Related U.S. Application Data

[62] Division of Ser. No. 370,540, Jan. 9, 1995.

[51] Int. Cl.$^6$ .................................................. H01R 13/00
[52] U.S. Cl. ............................................ 439/500; 429/99
[58] Field of Search ................................... 439/500, 505, 439/506, 627; 429/96, 97, 98, 99, 100

[56] References Cited

U.S. PATENT DOCUMENTS

| | | | |
|---|---|---|---|
| 4,815,980 | 3/1989 | Lauder et al. | 439/627 |
| 5,127,849 | 7/1992 | Karl et al. | 439/500 |
| 5,203,709 | 4/1993 | Huang | 439/38 |
| 5,294,497 | 3/1994 | Muramatsu et al. | 429/97 |
| 5,312,269 | 5/1994 | Hwang | 439/627 |
| 5,421,743 | 6/1995 | Hwang | 439/500 |
| 5,431,575 | 7/1995 | Engira | 439/500 |
| 5,505,635 | 4/1996 | Willows et al. | 439/500 |
| 5,537,022 | 7/1996 | Huang | 429/99 |
| 5,707,249 | 1/1998 | Byrd | 439/500 |

*Primary Examiner*—Gary F. Paumen
*Assistant Examiner*—Tho D. Ta
*Attorney, Agent, or Firm*—Hymen Diamond; Clifford A. Poff

[57] ABSTRACT

A frame for a cabinet for a deodorant particularly for commodes and urinals in public facilities. The frame is composed of separate back plate, top member and bottom member composed of a resilient plastic. The top member and bottom member are snap-locked to the back plate and secured further by projections from the top and bottom members in slots in the back plate. The bottom member is a liquidtight tray capable of processing deodorants in bottles through wicks or can with wicks, absorbent surcotas and wafers. There is a bottle holder snap-locked to the underside of the top member. A battery-blower assembly is snap-locked to the back plate. The battery poles are joined to the wires from the blower-motor by a clip. The tube which drips deodorant into a commode or urinal is secured to the outlet from the tray by ribs and bulkhead fittings are dispensed with.

13 Claims, 4 Drawing Sheets

ELECTRICAL CONNECTOR

REFERENCE TO RELATED APPLICATION

This application is a division of application Ser. No. 08/370,540, filed Jan. 9, 1995, for INTEGRATED FRAME ASSEMBLY FOR DEODORANT CABINET AND ASSIGNED TO PESTCO. INC.

BACKGROUND OF THE INVENTION

This invention relates to electrical connectors and it has particular relationship to connectors for interconnecting a battery and a device such as a motor energized from a battery. A typical embodiment of this invention is disclosed in the parent application Ser. No. 08/370,540.

In apparatus of the general type disclosed in the parent application, the practice in accordance with the teachings of the prior art has been to join the battery to the motor electrically by soldering the terminals. Usually an electrical conductor, for example, a wire, from the motor is soldered to a pole of the battery. This practice has presented difficulty particularly in the confined space available and it has been costly requiring personnel with the usual mask and soldering facilities. The soldered joints have at times proven to be unreliable.

It is an object of this invention to overcome the above-described difficulties and disadvantages of the prior art and to provide a solderless electrical joint between components, such as the motor and the battery of the apparatus disclosed in the parent application, to be electrically connected.

SUMMARY OF THE INVENTION

In accordance with this invention there is provided small clip assemblies which serve as battery contacts and grip the motor wires that protrude at the base of the battery holder. Soldering is thus eliminated. Each clip assembly includes a slotted member which is integrally a part of the plastic supporting structure of a battery blower unit energized by the battery. Typically, the slotted member has the shape of a structural channel, or of a member of generally C transverse cross section, with slots formed of flanges along one dimension. A metal strip is held within the member by flanges. Near one end, the slotted member has a hole through which the exposed end of the wire from the device to be energized, the motor of the blower unit, protrudes to engage the metal strip electrically. Near the opposite end, the metal strip is provided with a projection for connection of the adjacent pole of the battery. Where necessary, the flanges of the member are spaced to permit the penetration of the adjacent pole of the battery to engage electrically the projection.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which:

FIG. 4 is a view in transverse section taken along line IV—IV of FIG. 3;

FIG. 5 is a view in partial longitudinal section taken along line V—V of FIG. 3;

FIG. 6 is a fragmental view partly in section showing the connection in the practice of this invention of a motor terminal wire at its point of contact to the battery with a metal clip and without soldering.

DETAILED DESCRIPTION OF EMBODIMENT

Figure 1:
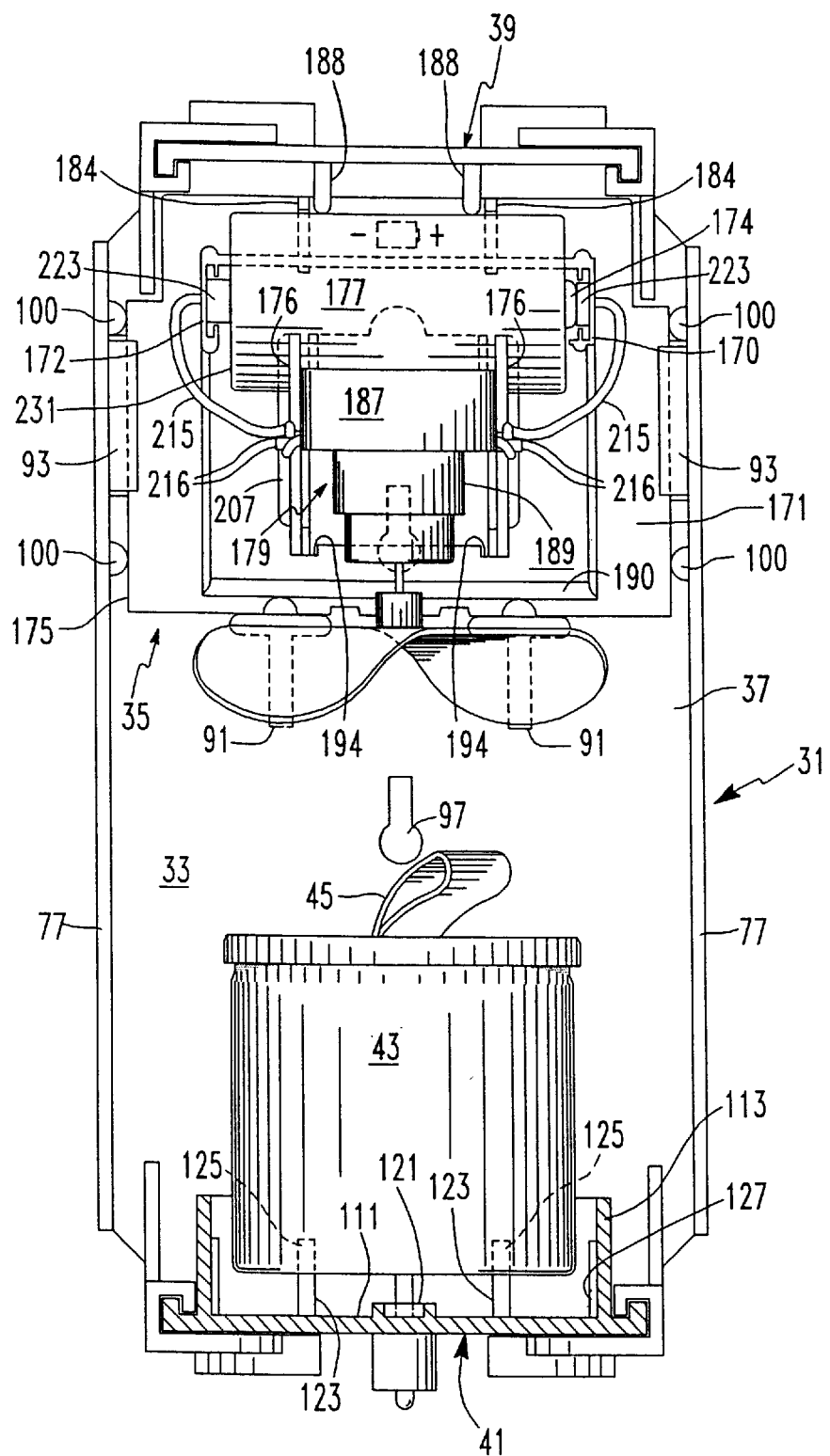
FIG. 1 is a view in front elevation showing apparatus disclosed in the parent application which embodies the invention of this application.

The apparatus disclosed in the drawings is an integrated frame assembly 31 for supporting the housing of a cabinet containing facilities for dispensing a deodorant or a disinfectant or the like, particularly in the rest rooms of a public institution. This apparatus includes an embodiment of this invention and is presented here to aid in the understanding of this invention. The assembly 31 includes a frame 33 and a battery-blower unit 35 (FIG. 2) mounted on the frame 33. The frame 33 includes a back plate 37, a top member 39 and a bottom member 41 which is essentially a liquid-tight tray. In FIG. 1 a can 43 of a deodorant which has a wick 45 that absorbs the deodorant is shown. The deodorant in the wick is vaporized by a stream of air from the battery-blower unit 35. The can 43 is one of a number of facilities for producing a deodorant or like vapor which the apparatus 31 is adapted to process.

The back plate 37 has ramps 91 and runners 93 for securing the battery-blower unit and openings 95, 97 for mounting the frame 31 on a wall. On the internal surface of projections 77 on the back plate 37 which are provided to strengthen it, there are spacers 100 (FIG. 3) for aligning the battery-blower unit 35.

The bottom member 41 is a liquid-tight tray. In the center of the tray there is a ring 121. A plurality of studs 123, 125 and 127 arrayed in rows generally perpendicular to each other project upwardly from the base 111. The studs 123 are short and the studs 125 which are near the corners of the array are longer.

Figure 3:
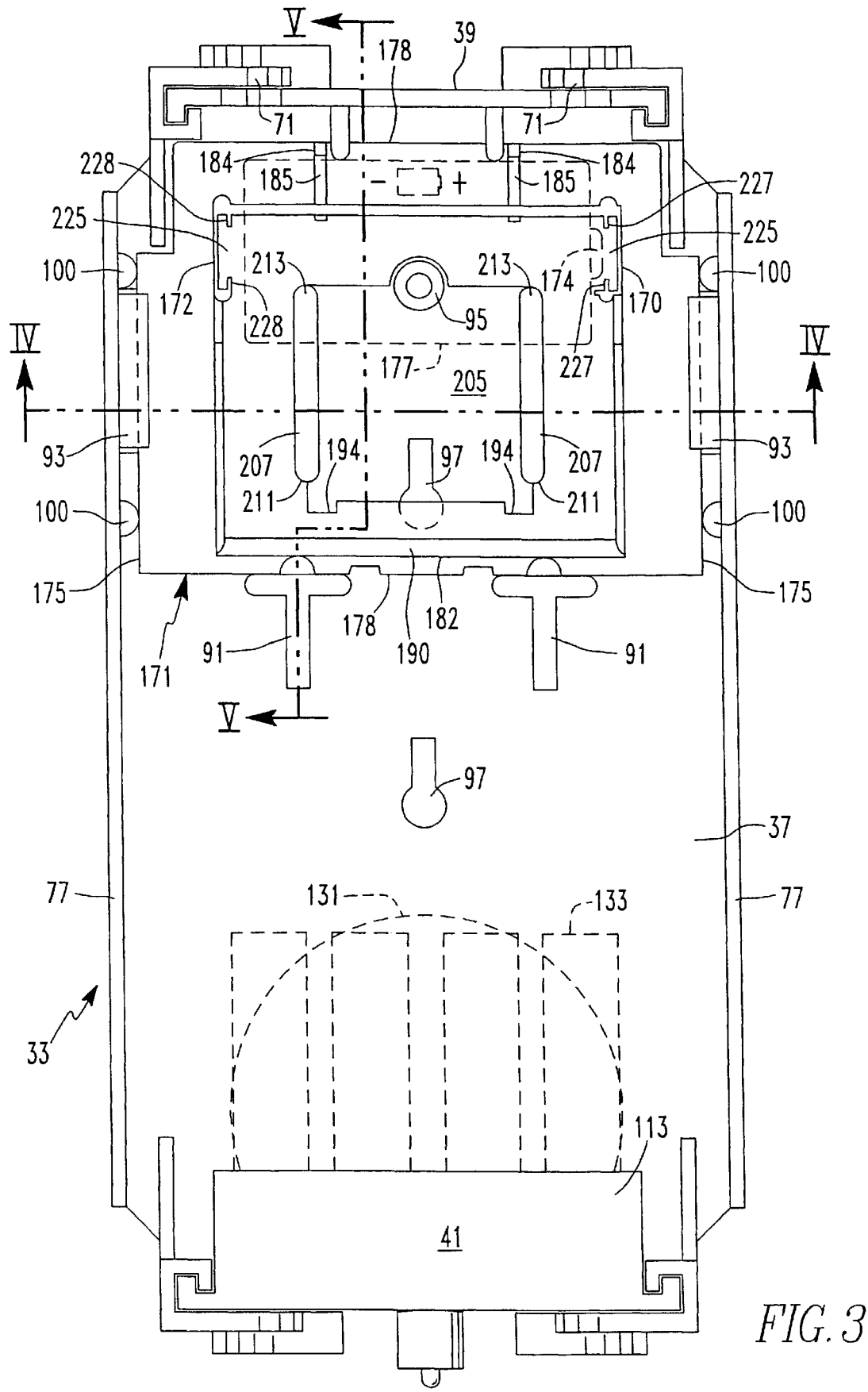
FIG. 3 is a view in front elevation of the frame showing the facilities for mounting the electrical connector in accordance with this invention as part of the battery-blower unit.

FIG. 1 shows the can 43 supported on the short studs 123 and spaced from the walls 113 by being nested in the upward projecting studs 125 in the corners (FIG. 1). The can 43 is thus prevented from moving. The air which vaporizes the liquid in the wick thus has space for unobstructed flow of air. As shown in FIG. 3, ceramic discs 131 are mounted in one orientation and wafers 133 are mounted in an orientation at right angles to the discs 131. The ceramic discs 131 and wafers 133 are spaced by the studs so that air circulates from the battery-blower unit 35 contacts these components on all sides to diffuse the deodorant vapors. Studs 123 in a rectangular array, and studs 125 are provided to position and hold erect the wafers 133, typically four in number, aligned and ceramic discs 131, typically three in number, aligned generally at right angles to the wafers. FIG. 3 (bottom) illustrates an alternative to the can 43 which can be used in the practice of this invention.

The battery-blower unit 35 (FIG. 2) includes the supporting plate 171 and the battery-motor bracket 173. The supporting plate 171 is rigidly mounted on the back plate 37. The outer sides 175 of the supporting plate 171 are thrust upwardly through the runners 93, while the inner surface of the plate at the bottom rides on the ramps 91 (FIG. 1). This inner surface is flexed and is under stress when insertion takes place. When the inner surface of the plate 171 springs from the ramps 91, the plate 171 is snap-locked to the back plate 37. The runners 93 and the plate 171 at its ends are a tight fit so that the passage of the ends of the plate through the runners is resisted and the plate 171 is flexed. Once plate 171 is fully positioned in the runners, it relaxes producing a snap-lock. The plate 171 is also held by pins 188 which extend from top member 39 (FIGS. 1, 5). The plate 171 is aligned by the spacers 100 in the projections 77 of back plate 37.

Near the top of plate 171 channels 170 and 172 extend from opposite ends of support plate 171 spaced a short distance outwardly from positive pole 174 (FIG. 1) and the negative pole (not shown) respectively. The flanges 227 of channel 170 are spaced further apart than the flanges 228 (FIG. 2) of channel 172 to permit the necessary close spacing of channel 170 and the protruding positive pole 174 (FIG. 3). This structure also precludes improper positioning of the battery. If an attempt were made to position the battery with the negative pole opposite channel 170, there would be no contact with negative battery terminal, necessitating correct polarization for operation of the battery-blower unit 35.

Figure 2:
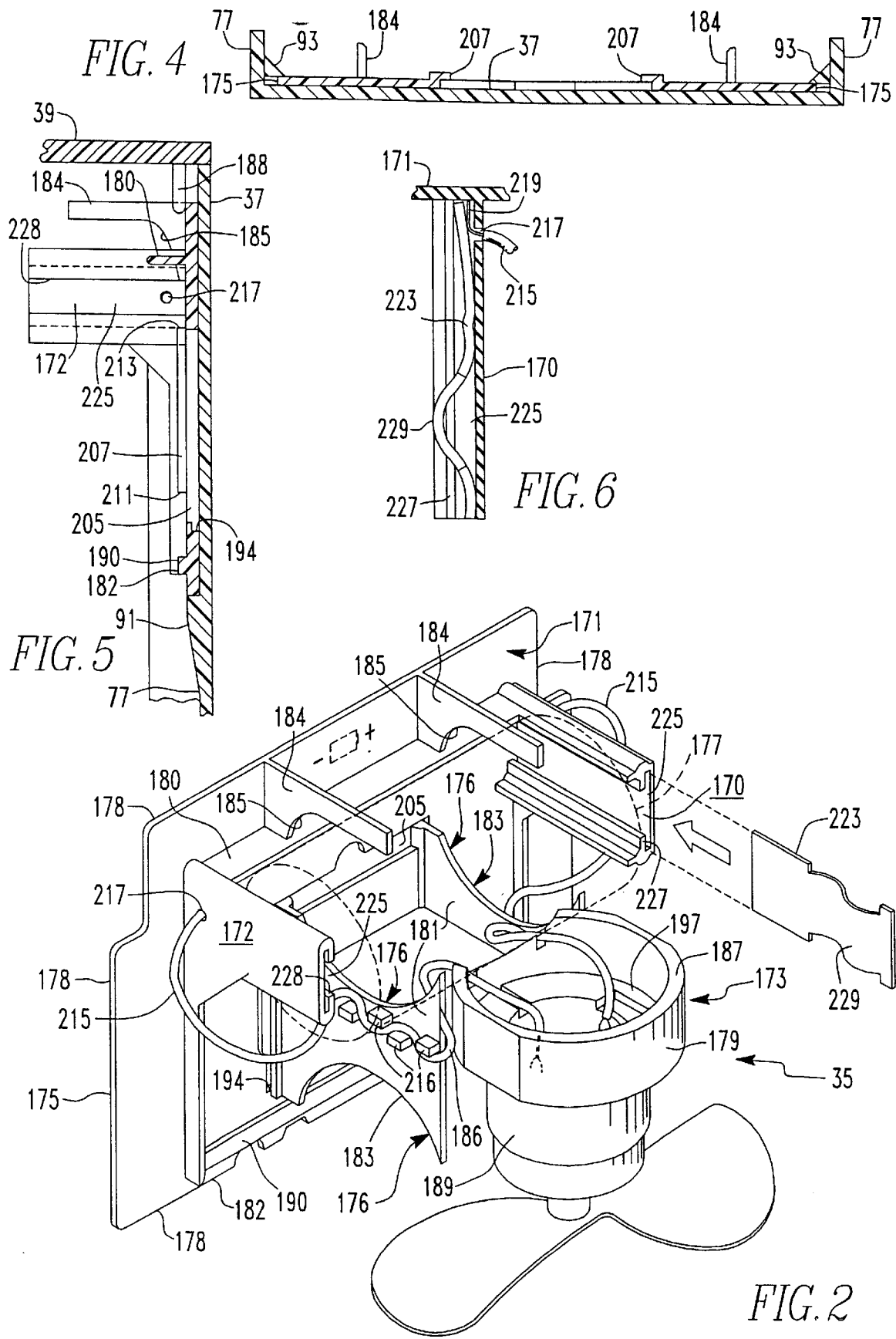
FIG. 2 is a view in isometric showing the complete battery-blower unit in which this invention is integrated.

The battery-blower bracket 173 includes a cradle 176 for the battery 177. A motor socket unit 179 extends from the cradle 176. The cradle 176 includes plates 181 whose opposite vertical surfaces 183 are arcuate to provide seats for the battery 177. The arcuate seats 183 for the battery 177 in opposite surfaces constitute a cradle for the battery in each of opposite mountings of the battery-blower bracket 173. To hold the battery 177 securely, the supporting plate 171 is provided with holding bars 184 which have curved edges 185 to match the contour of the battery. The holding bars 184 are seated in the right angle joint formed between the outer perimeter 178 of the supporting plate 171 and projecting shelf 180 part of a frame-like structure 182 internally of plate 171. The motor socket unit 179 is supported by projections 186 (FIG. 2) connected to the outer ends of the plates 181. The motor-socket unit 179 includes a socket 187 for a motor of larger dimensions and a socket 189 for a motor 191 of smaller dimensions. In FIG. 2 a motor 191 is shown in its socket 189.

Figure 7:
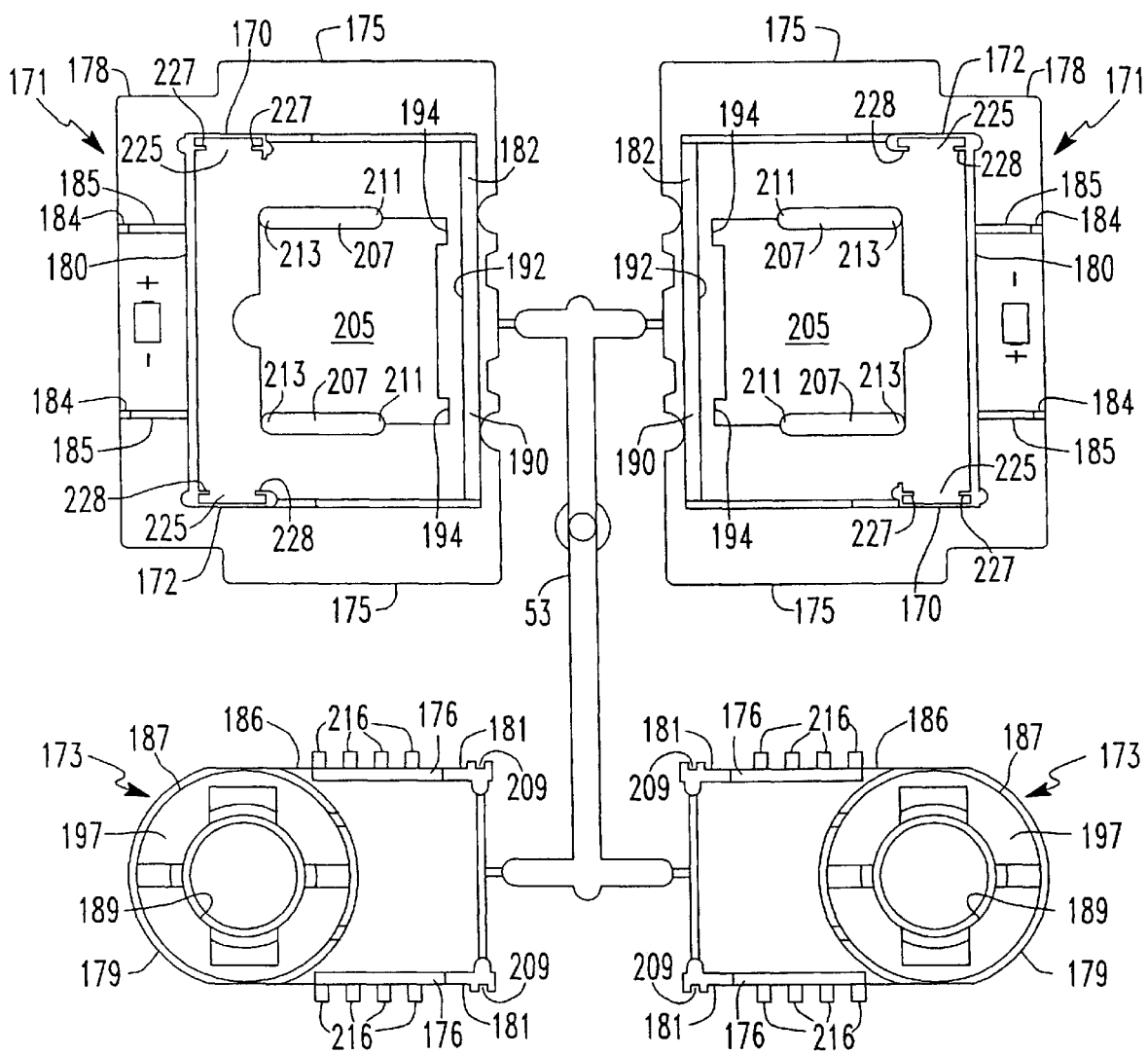
FIG. 7 is a plan view showing the blower assembly support as it is completed and removable from twin molds.

The supporting plate 171 has a generally central opening 205 having a generally rectangular boundary. Along opposite vertical sides of the boundary there are tracks 207. The tracks 207 extend only partly along the opposite sides (FIG. 7). At the end of the battery-motor bracket 173, remote from the socket unit 179, the bracket has opposite slots 209 (FIG. 7) dimensioned and spaced to engage the tracks 207. To mount the battery-blower bracket 173 on the supporting plate 171, the slots 209 are engaged with the track 207 at the points 211 where the tracks terminate, i.e., at the bottom when the supporting plate is mounted on the back plate 37, and are moved along the tracks (FIG. 3). When the slots 209 reach the ends 213 of the tracks 207, they are stopped by the body of the supporting plate 171. The slots 209 are a tight fit on the track 207 and they are stressed while being moved. When the movement is stopped, the slots are relaxed and the bracket 173 is snap-locked on the support plate 171. In addition, the slotted members 209 are forced over the lower bar 190 of the frame 182 and when they clear the inner end of the bar 190 spring into snap lock state. The forced movement of the bracket continues and the ends of the slot 209 spring over edge 194 producing an additional snap lock. The slots 209 are interchangeable with the tracks 207 so that the bracket 173 can be mounted with the socket 189 below the socket 187 or the socket 189 above and the socket 187.

The channels 170 and 172 extending integrally from support plate 171 serve to connect the leads or wires 215 from motor 191 or a motor in the socket 187 to the battery 177. The wires 215 are guided by nubbins 216 on plates 181 of battery cradle 176 (FIGS. 2, 7). Each channel 170 and 172 has a hole 217 in its inner end (FIG. 5). The stripped end 219 of each wire 215 from the motor terminals (not shown) is passed through this hole (FIG. 6) and extends inwardly of the channels 170 and 172. A metal strip 223 (FIG. 2, 6) is inserted in the slots 225, formed by the flanges 227 and 228 of the channels. Each strip 223 firmly engages the stripped end 219 of a wire 215. The strip 223 has a bulge 229 (FIG. 6) which engages the adjacent pole 174 of the battery. Each wire is thus connected to a pole of the battery.

As shown in FIG. 7, the supporting plate 171 and the battery-motor unit 173 are formed in twin molds. The components 171 and 173 are formed typically of a material such as acrylic butylene and styrene. This material serves to produce a structure of greater strength than the polypropylene fiberglass typical of the material from which the other components such as the back plate 37, the top member 39 and the bottom member 41 are formed. The additional strength is necessary because the components 171 and 173 are subjected to higher stresses by the moving parts which they support. The components 171 and 173 are positioned in the mold so that they can be readily removed and snapped together to produce a sturdy motor-battery holder assembly.

While preferred embodiments of this invention have been disclosed herein, many modifications thereof are feasible. This invention is not to be restricted except insofar as is necessitated by the spirit of the prior art.

We claim:

1. The combination of a battery having poles and a wire to be connected to apparatus to be energized by said battery, a solderless connector for connecting said wire to said battery; said connector including a member of electrically insulating material having an aperture for receiving said wire, an electrically conductive elongated strip supported within said member for connecting one side of said wire to said strip physically in electrically conductive relationship, and means on said strip for connecting a pole of said battery to said strip.

2. The combination of claim 1 wherein the member is channel shaped having overhanging flanges along one dimension of the strip, said flanges of said member engaging the strip to effectuate the physical disposition of said strip in said member.

3. The combination of claim 1 wherein the member is composed of acrylic butylene styrene.

4. An electrical connector for connecting first electrical apparatus to second electrical apparatus including a member of insulating material having a slot therein, a strip of electrically conductive material in said slot, said member having an opening affording access to said strip, a wire of electrically conductive material connected to said first apparatus, said wire penetrating through said opening in said member with its penetrating end in electrical contact with said strip, and means connected to said second apparatus for connecting said second apparatus to said strip in electrical contact therewith thereby to connect said second apparatus in an electrical circuit with said first apparatus, the electrical contact between said end of said wire.

5. The electrical connector of claim 4 for connection of the wire to the pole of a battery, said battery constituting the second apparatus, wherein the strip has a projection for connection to the pole of said battery to the opposite face of said strip.

6. The electrical connector of claim 4 wherein the second apparatus is a battery having a pole, and the pole extends into the slot in contact with the electrically conducting strip.

7. A solderless connector including a member composed of electrically insulating material having a slot therein and having an opening extending into said slot, a strip of electrically conductive material in said slot, a wire of electrically conductive material having an electrically conductive end penetrating through said opening with said end in electrical contact with one face of said strip, the opposite face of said strip being adapted to be contacted by an electrical conductor to form electrical contact to said wire.

8. The solderless connector of claim 7 wherein the member of electrically insulating material is composed of acrylic butylene and styrene.

9. The solderless connector of claim 7 wherein the strip is slideably connected to the member.

10. The solderless connector of claim 7 wherein the member is in the shape of a structural channel having opposite flanges along a dimension thereof and the strip is held in said member by engagement under said flanges.

11. A device for use in energizing apparatus from a battery of generally cylindrical structure having a first pole and a second pole, said first pole projecting outwardly from one end of said battery; the device including a support plate having oppositely disposed first and second members of insulating material, each having the shape of a structural channel having flanges extending therefrom, said flanges of each said member defining a slot, an electrically conductive strip in each slot, the flanges of said first member being spaced a greater distance than the flanges of the second member so as to receive the battery between said first and second members with the first projecting pole extending into the slot defined by the flanges of the first member in contact with the electrically conductive strip in the slot of said first member and with said second pole in contact with the electrically conductive strip of the second member, whereby the battery can be positioned only in the one position defined for effectively energizing said apparatus.

12. The combination of claim 11 wherein each strip has a bulge in the surface contacted by the respective poles of the battery.

13. A device for use in energizing apparatus from a battery of generally cylindrical structure having a first pole and a second pole, said first pole projecting outwardly from one end of said battery; the device including a support plate having oppositely disposed first and second members of insulating material, each having the shape of a structural channel having flanges extending therefrom, said flanges of each said member defining a slot, an electrically conductive strip in each slot, the flanges of said first member being spaced a greater distance than the flanges of the second member so as to receive the battery between said first and second members with the first projecting pole extending into the slot defined by the flanges of the first member in contact with the electrically conductive strip in the slot of said first member and with second pole in contact with the electrically conductive strip of the second member, whereby the battery can be positioned only in the one position defined for effectively energizing said apparatus, said apparatus to be energized, being energized by wires to be connected to the battery; and said each member of insulating material having a hole permitting penetration of the corresponding wire into contact with the surface of the corresponding electrically conductive strip which surface is opposite to the surface to be contacted by the poles of said battery.

* * * * *